United States Patent
Giunta et al.

(10) Patent No.: US 9,921,129 B2
(45) Date of Patent: Mar. 20, 2018

(54) METHOD AND SYSTEM FOR THE CONTINUOUS REMOTE MONITORING OF DEFORMATIONS IN A PRESSURIZED PIPELINE

(71) Applicant: ENI S.p.A., Rome (IT)

(72) Inventors: Giuseppe Giunta, San Donato Milanese (IT); Francesco Bertoncini, Borgo a Mozzano (IT); Florin Octavian Turcu, Cesson-Sevigne (FR); Marco Raugi, Pisa (IT)

(73) Assignee: ENI S.p.A., Rome (IT)

( * ) Notice: Subject to any disclaimer, the term of this patent is extended or adjusted under 35 U.S.C. 154(b) by 370 days.

(21) Appl. No.: 14/688,287

(22) Filed: Apr. 16, 2015

(65) Prior Publication Data

US 2015/0300909 A1 Oct. 22, 2015

(30) Foreign Application Priority Data

Apr. 18, 2014 (IT) .............................. MI2014A0734

(51) Int. Cl.
| | |
|---|---|
| *G01M 5/00* | (2006.01) |
| *G01H 1/00* | (2006.01) |
| *G01N 19/00* | (2006.01) |
| *G01M 7/00* | (2006.01) |
| *G01B 17/04* | (2006.01) |

(52) U.S. Cl.
CPC ........... *G01M 5/0025* (2013.01); *G01B 17/04* (2013.01); *G01H 1/00* (2013.01); *G01M 5/0066* (2013.01); *G01M 7/00* (2013.01); *G01N 19/00* (2013.01)

(58) Field of Classification Search
CPC ............. G01M 5/0025; G01M 5/0033; G01M 5/0041; G01M 5/0058; G01M 5/0066
See application file for complete search history.

(56) References Cited

FOREIGN PATENT DOCUMENTS

| | | |
|---|---|---|
| GB | 2 475 225 | 5/2011 |
| WO | WO 2014/096019 A1 | 6/2014 |

OTHER PUBLICATIONS

Bernasconi et al., Pipeline Acoustic Monitoring, 2012, 7th Pipeline Technology Conference, 7 pp.*

(Continued)

*Primary Examiner* — Toan Le
(74) *Attorney, Agent, or Firm* — Oblon, McClelland, Maier & Neustadt, L.L.P.

(57) ABSTRACT

A method and system are described, for the continuous remote monitoring of deformations in a pipeline (10) suitable for the transportation of a pressurized fluids, such as, for example, pipelines designed for the transportation of low- and high-pressure fluids (natural gas, crude oil, water, oil products) that cannot be controlled by using Intelligent Pipeline Inspection Gauge (PIG) systems, or sections of pipeline exposed to the risk of landslides and/or earthquakes in which catastrophic breakages can be generated, with a consequent interruption in the transportation service. The method and system envisage the application of the guided wave technique for the remote-controlled monitoring of the tensional state of the pipeline (10) also on extensive sections, having a length equal to hundreds of meters, using a relatively reduced number of sensors (12) installed on the outer surface of the pipeline (10).

10 Claims, 10 Drawing Sheets

(56) References Cited

OTHER PUBLICATIONS

Umeadi et al., The Development of an Intelligent Sensor for the Monitoring of Pipeline System Integrity, Oct. 28-30, 2008, 2008 SPE Russian Oil & Gas Technical Conference and Exhibition, Moscow, Russia, 10 pp.*
Italian Search Report dated Jul. 24, 2014 in Italian application MI20140734, filed on Apr. 18, 2014 ( with English Translation of categories of cited documents).
M.F. Shehadeh et al. "Buckling detection within subsea pipeline laying using Acoustic Emission technique", EWGAE 2010, XP-002727750, 2010, 8 pages.

* cited by examiner

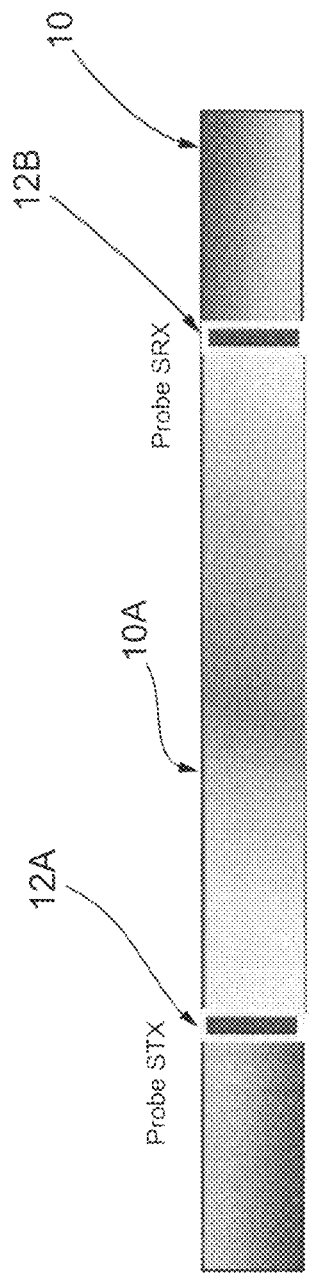
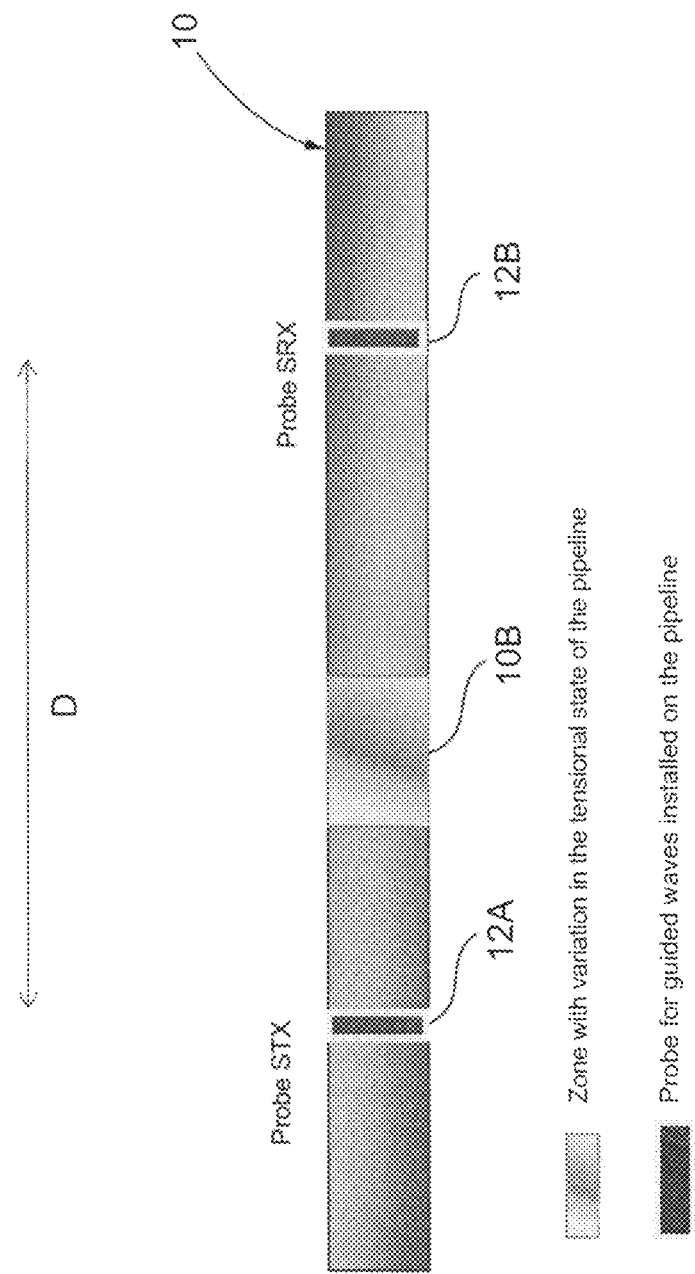

METHOD AND SYSTEM FOR THE CONTINUOUS REMOTE MONITORING OF DEFORMATIONS IN A PRESSURIZED PIPELINE

CROSS-REFERENCE TO RELATED APPLICATIONS

The present application is based upon and claims the benefit of priority from Italian Patent Application No. MI2014A000734, filed Apr. 18, 2014, the entire contents of which are incorporated herein by reference.

BACKGROUND OF THE DISCLOSURE

1. Field of the Disclosure

The present invention relates to a method and system for the continuous remote monitoring of deformations in a pressurized pipeline.

In particular, the present invention mainly relates to operating pipes designed for the transportation of low- and high-pressure fluids (natural gas, crude oil, water, oil products) that cannot be controlled by using Intelligent Pipeline Inspection Gauge (PIG) systems, or sections of pipeline exposed to the risk of landslides and/or earthquakes in which catastrophic breakages can be occurred, with a consequent interruption of the transportation service.

2. Description of the Related Art

Among the systems currently used, usable or simply proposed for measuring extensive deformations of a pressurized pipeline, two distinct types can be substantially identified:
  indirect systems that control the integrity of the pipeline through measurements of the movement of the surrounding land, among which inclinometers, extensometers with vibrating strings, piezometers and satellite systems can be mentioned; and
  direct systems or, in other words, applied directly to the pipelines, among which extensometers applied locally and systems based on optical fibers, can be mentioned.

Inclinometers are devices which are installed in the soil, in the immediate proximity of the pipeline, to reveal any possible ground movements. The inclinometers are normally positioned inside concrete wells which, however, can be destroyed by possible landslides. Extensometers with vibrating strings are systems installed in the ground for detecting substantial movements of the land surrounding the pipeline. Depending on the embodiment, extensometers with vibrating strings can be defined as "quadrilaterals".

Piezometers are systems installed in the soil which estimate the pressure of the surrounding water and draining efficiency. A substantial accumulation of water in the land surrounding the pipeline can in fact indicate the possible occurrence of a landslide. Finally, a satellite system for the remote monitoring of underground pipelines is described, for example, in the document WO 2010/099881A1 filed by the same Applicant.

Extensometers locally applied can directly measure the tensional state of the pipeline. Three extensometers are usually installed at each measurement point, on angular positions 120° distant and oriented for measuring the axial deformation of the pipeline. The data acquired provide information relating to the deformations present around the section of the pipeline where these extensometers are installed.

Measurement systems of the tensional state based on optical fibers are systems distributed along the pipelines for monitoring underground extending sections even for tens of kilometers. A typical example of an embodiment of these systems is based on the light scattering phenomenon according to the Brillouin effect. Scattering is an intrinsic phenomenon of light propagation in silicon-based materials of which optical fibers are composed. The Brillouin effect therefore produces a well-known reply to external temperature or elastic deformation variations in the material with which the pipeline is constructed.

All the monitoring systems described above are passive systems capable of measuring movements of the land surrounding the pipeline or, as in the case of extensometers locally installed, deformations induced by landslides. Systems which measure movements of the land surrounding pipelines in areas potentially seismic or with the possibility of landslides, do not provide direct information on the integrity of the pipeline, but only qualitative data correlated with movements of a geological site.

As far as extensometers are concerned, these are probes installed locally, which are not capable of providing volume information on the state of integrity of relatively long sections of pipeline. Vice versa, the probes of the system according to the present invention are capable of providing in continuous, if used in pairs, the screening of the elastic deformations of a section of pipeline having a length in the order of tens of meters. Furthermore, both systems based on optical fibers and extensometers locally installed are sensitive to potential physical damage caused by landslides or other geological/seismic movements.

BRIEF SUMMARY OF THE DISCLOSURE

A purpose of the present invention is therefore to provide a method and system for the continuous remote monitoring of deformations in a pressurized pipeline, capable of solving the drawbacks of the known art described above, in an extremely simple, economical and particularly functional way.

The method and system for the continuous remote monitoring of deformations in a pressurized pipeline according to the present invention, can be used for identifying deformations induced by landslides or earthquake phenomena affecting the pipeline for sections having a length in the order of tens if not hundreds of meters. In particular by using the method proposed the curvatures and crush zones of the pipelines can be detected. In addition to this, the system used for detecting extensive deformations is also capable of revealing geometrical and elastic deformations of the local type, such as for example buckling phenomena or localized corrosion phenomena.

The system according to the invention envisages the installation of sensing probes of both passive and active type, on pipelines that require a long term monitoring. This system is capable of ensuring precision and repeatability of the measurements, in addition to simplicity and affordability of the installation of the distributed sensors discretely along the pipeline. The possibility of carrying out remote passive monitoring guarantees non-interference with the operating activities of the line, providing extremely reliable results in terms of reliability of the monitoring system.

More specifically, the objectives and advantages of the method and system for the continuous remote monitoring of deformations in a pressurized pipeline according to the present invention are the following:

possibility of monitoring relatively long sections of a pipeline by using a limited number of sensors;

possibility of detecting and controlling with time, not only local variations, in the sense of small deformations, but also extensive variations in the volume of the pipeline in term of the tensional state of pipeline itself;

possibility of providing a continuous "intelligent" monitoring of the pipeline, based on a continuous comparison between a numerical model and experimental measurements;

through a periodic comparison between the measured data in a given moment in time $t_0$ and those measured in a subsequent moment in time, $t_0+n*\Delta t$, the possibility of updating the numerical model of the pipeline and, at the same time, dynamically defining the alarm thresholds;

possibility of detecting extensive deformations along an underground pipeline and assessing the tensional state generated in the material (steel) of said pipeline by movements of the ground, even if barely visible on the surface, anticipating a possible breakage;

possibility of monitoring more extensive sections of pipeline with the same number of sensors, using the same in both "pulse-echo" mode (reflection of the guided wave) and in "pitch-catch" mode (transmission of the guided wave);

contemporaneous use of a wide variety of information for evaluating the state of integrity of the pipeline, among which, due to the deformed or pressurized section, variation in the speed of transmitted wave propagation with a consequent variation in the transit time of a section of pipeline having a prefixed length, possible lack of propagation or partial propagation of the transmitted wave, modification of the waveform of the pulse transmitted (variation in the width and/or phase and/or duration);

thanks to the continuous monitoring, the possibility of following the dynamics of the changes revealed in the transmitted or reflected wave and relating them with the movements of the surrounding land.

These objectives according to the present invention are achieved by providing a method and system for the continuous remote monitoring of deformations in a pressurized pipeline as specified in the independent claims.

Further characteristics of the invention are highlighted in the dependent claims, which are an integrant part of the present description.

BRIEF DESCRIPTION OF THE SEVERAL VIEWS OF THE DRAWINGS

The characteristics and advantages of a method and a system for the continuous remote monitoring of deformations in a pressurized pipeline according to the present invention will appear more evident from the following illustrative and non-limiting description, referring to the enclosed schematic drawings in which:

FIGS. 3A and 3B show the variation in the tensional state of a section of pipeline monitored by two guided-wave sensors, where a variation extended to a whole surveyed section (FIG. 3A) is compared with a localized variation within such a surveyed section (FIG. 3B);

DETAILED DESCRIPTION OF THE DISCLOSURE

With reference to the figures, these show a method and guided-wave system for the continuous remote monitoring of deformations in a pressurized pipeline, indicated as a whole with the reference number 10. The guided waves are generated in the form of elastic vibrations by one or more sensors or probes 12 applied locally on an outer section 10A of the pipeline 10 being inspected. The wave propagation takes place using the wall of the pipeline 10, itself as a guiding structure.

Figure 1:
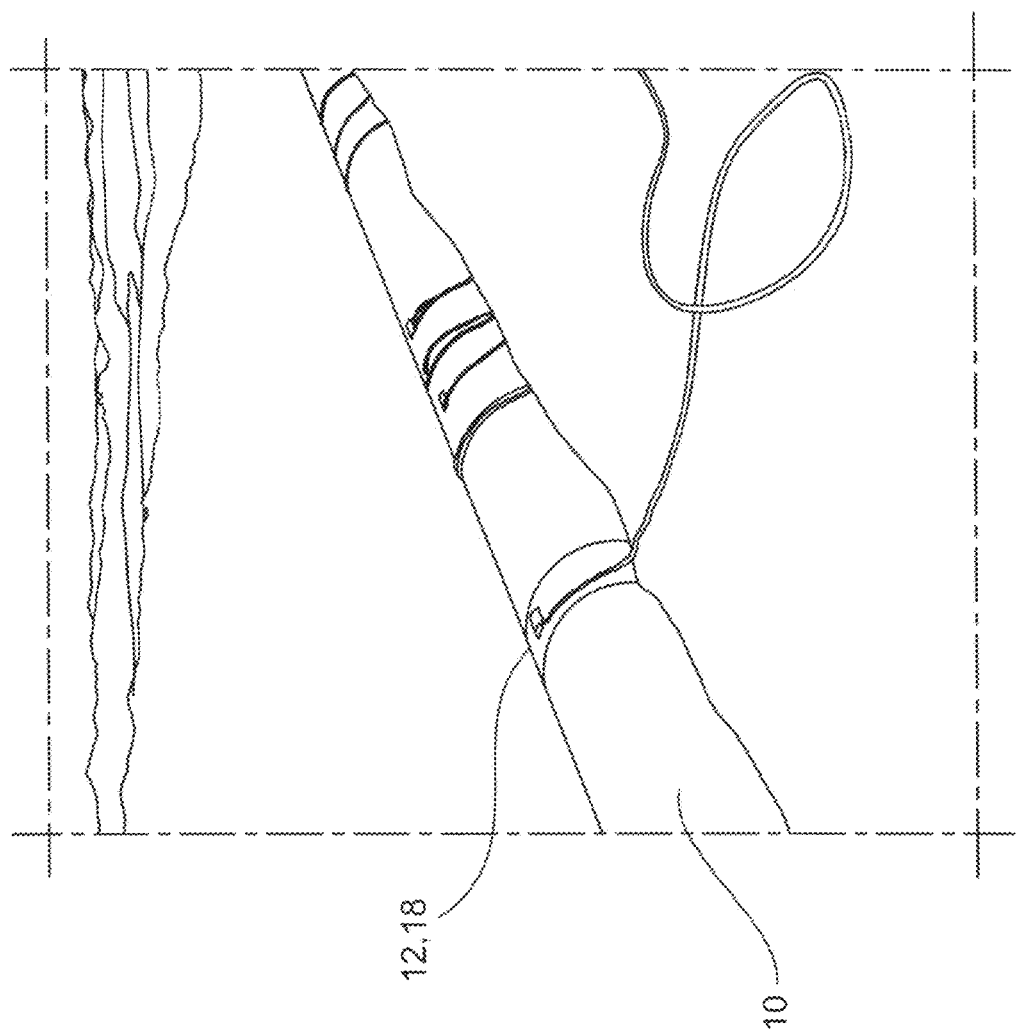
FIG. 1 is a schematic view which shows a generic buried pipeline to which a guided-wave monitoring system with magnetostrictive sensors according to the present invention, has been applied.

Each sensor 12 can be a magnetostrictive or piezoelectric type and can be capable of both triggering the guided wave (TX mode, transmitting sensor), and recording the passage of said guided wave (RX mode, receiving sensor). FIG. 1, for example, shows a guided-wave system based on sensors 12 of the magnetostrictive type applied to a 48 inches pipeline 10, under the ground for transporting natural gas.

Two modes of use of the guided-wave sensors 12 are possible:

pulse-echo mode: a single sensor 12, operating in TX-RX mode, emits the pulse and registers its echo;

pitch-catch mode: two sensors 12A and 12B installed at different points of the pipeline 10 are envisaged, of which a first 12A of said sensors acts as a transmitter and a second 12B of said sensors acts as a receiver.

The elastic wave generated at a point of the pipeline 10 can propagate up to distances in the order of tens of meters from the same point in which said elastic wave was generated. The elastic propagation of guided waves in the pipeline 10 is depending by the physical and geometrical characteristics of the pipeline-external means system. Every variation in these characteristics produces some variations in the propagation of the guided wave itself:

- modifying the amplitude, the form and/or the energy of the pulse that propagates;
- generating a reflected wave and a transmitted wave which, in turn, propagate from the point of origin of the physical variation encountered (defect or discontinuity) along the pipeline 10.

Among variations in the physical characteristics of the pipeline 10 for transporting fluids of which measurement methods with guided wave system are known, the following defects can be mentioned:

- presence of local defects;
- presence of local corrosion;
- local variation in the coating properties of the pipeline 10.

The monitoring system with guided waves allows local discontinuities along the pipeline 10 to be detected and localized through measuring the reflected elastic wave amplitudes and processing the propagation times between the point of anomaly and the measurement point. The purpose for using this system is therefore to detect and localize any possible defect along the pipeline 10 being inspected, and also to identify and measure each defect.

The detection and localization of defects require distinguishing and recognizing the signal due to the defect from signals generated by noise and joints, bends and branches normally present in the pipeline 10. The identification and measurement of the defect require the reconstruction of the geometry of the same defect, as the relation between the geometry of the defect and signal measured is given by a function which is generally unknown due to the complexity of the problem.

The methods currently used are of the heuristic type. Among these, the calibration method is the simplest and most widely-used. In the development phase of the monitoring system, the response signals from known defects are acquired and processed in order to obtain calibration curves with a variation in the geometrical parameters of the defect (length, width, thickness) with which to compare the response acquired by the system.

Other inversion methods, recently proposed, are based on neural networks. In the learning process of the neural network, signals generated by known defects are used. In the prediction phase, the signal generated by an unknown defect feeds the neural network whose output determines an estimation of the geometry of the defect.

The non-destructive guided wave method and system for monitoring the pipeline 10 can be used for detecting local corrosion and/or defective phenomena in the pipeline 10 itself.

Guided waves of the torsional type are generally used, with frequencies within the range of 4 kHz to 128 kHz, preferably 8, 16 or 32 kHz. The method and system according to the invention allowed the mechanical deformation phenomena of the steel of the pipeline 10 to be revealed, due to the variation in the internal and/or external pressure of the pipeline 10 itself, such as to cause transformation from the elastic state to the plastic state of the material. The method and system according to the invention allow the tensional state of the pipeline 10 to be remote monitored also on extensive sections equal to hundreds of meters, using a relatively reduced number of sensors 12 installed on the outer surface of the pipeline 10.

Figure 2:
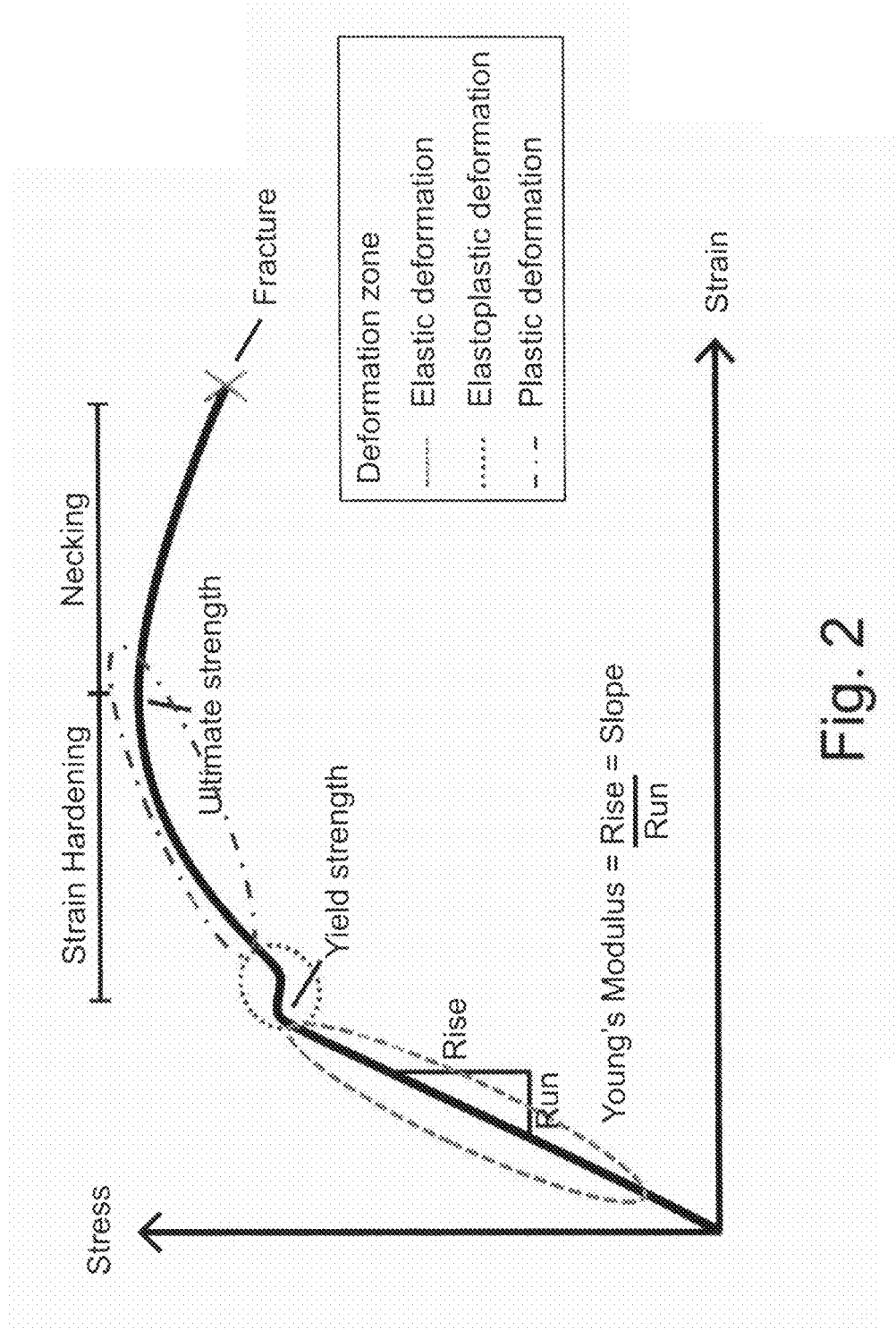
FIG. 2 is a diagram which shows the stress-deformation relation in the carbon steel with which pipelines are normally constructed.

FIG. 2 shows the relation between the stress σ and the deformation ε typical of carbon steels and shows the elastic deformation, elastic-plastic and plastic ranges, the yield point and break point. The method according to the invention is based on the possibility of detecting, with the guided wave system, the variation in the velocity of a guided wave which propagates in the section of pipeline 10 of interest, the variation in the wave velocity being sensitive to the variation in the elastic properties of the material.

In order to illustrate the method according to the invention, a homogeneous and isotropic section 10A of the pipeline 10 is considered (FIG. 3A), constructed in steel and characterized by the following physical parameters:

$E_0$=Young modulus;
$v$=Poisson number;
$\rho$=density

Two sensors 12A and 12B for guided waves are installed on the section of pipeline 10A considered. A first sensor 12A, or transmitting sensor, is capable of generating an elastic wave of the torsional type T(0,1), whereas a second sensor 12B, or receiving sensor, is capable of detecting the passage of said wave. The two sensors 12A and 12B are positioned at a predefined distance D, equal to the length of the section of pipeline 10A, and operate in pitch-catch mode.

Under ordinary conditions, the pressure inside and outside the pipeline 10 are such that the steel operates within the elastic range. In this situation, the velocity $c_{T0}$ of the guided wave generated by the transmitting sensor 12A and the time t0 used for transmitting along the section of length D are respectively equal to:

$$c_{T0} = \sqrt{\frac{E_0}{2(1+v)\rho}} \qquad t_0 = \frac{D}{c_{T0}}$$

with $E_0 = \frac{d\sigma'}{d\varepsilon}$.

If the external pressure on the pipeline increases so as to bring the steel within the elastic-plastic range, the wave velocity $c_T$ varies, with a consequent variation in the passage time t of the section of pipeline 10A having a length D. In other words, the variation in the tensional state of the pipeline 10 leads to a variation (delay) Δt in the time instant of the arrival at the receiving sensor 12B of the pulse generated by the transmitting sensor 12A:

$$\Delta t = t - t_0 = D \cdot \left( \frac{1}{c_T} - \frac{1}{c_{T0}} \right)$$

wherein $c_T = f(\sigma, \varepsilon)$.

This variation Δt can be measured, it does not depend on the frequency of the wave transmitted and will be greater, the greater the distance D between the two transmitting 12A and receiving 12B sensors and the more the $c_{T0}/c_T$ ratio differs from 1. The method according to the invention is therefore based on the correlation between the measurement of the variation Δt and the measurement of the variation in the tensional state of the pipeline 10.

Two particular cases can be illustrated. The first case envisages the hypothesis that the operating point in the elastic-plastic range is relatively "close" to the elastic range, so that it can be held that the propagation of the guided wave follows in a first approximation the specific propagation laws in the elastic range. In this first case, if:

$$E = E_0 + \Delta E, \text{ with } \left| \frac{\Delta E}{E_0} \right| < 1,$$

this gives $\frac{\Delta t}{t_0} \cong -\frac{1}{2} \frac{\Delta E}{E_0}$.

The second case, on the contrary, envisages the hypothesis that the variation in pressure on the pipeline 10 induces the steel to operate in the plastic range close to the breakage, i.e. where the material is no longer able to propagate the guided wave. This second case can also be detected by the guided wave system: for the pulse transmitted by the transmitting sensor 12A, there is in fact no pulse received by the receiving sensor 12B.

Finally, the method according to the invention can also be applied when the variation in pressure relates to a partial section 10B of pipeline between the two guided-wave sensors transmitting 12A and receiving 12B, as shown in FIG. 3B. In this case, the wave transmitted by the transmitting sensor 12A is partly reflected and partly transmitted by the discontinuity zone. These guided waves can be detected using the system proposed in pulse-echo and pitch-catch mode.

Figure 4:
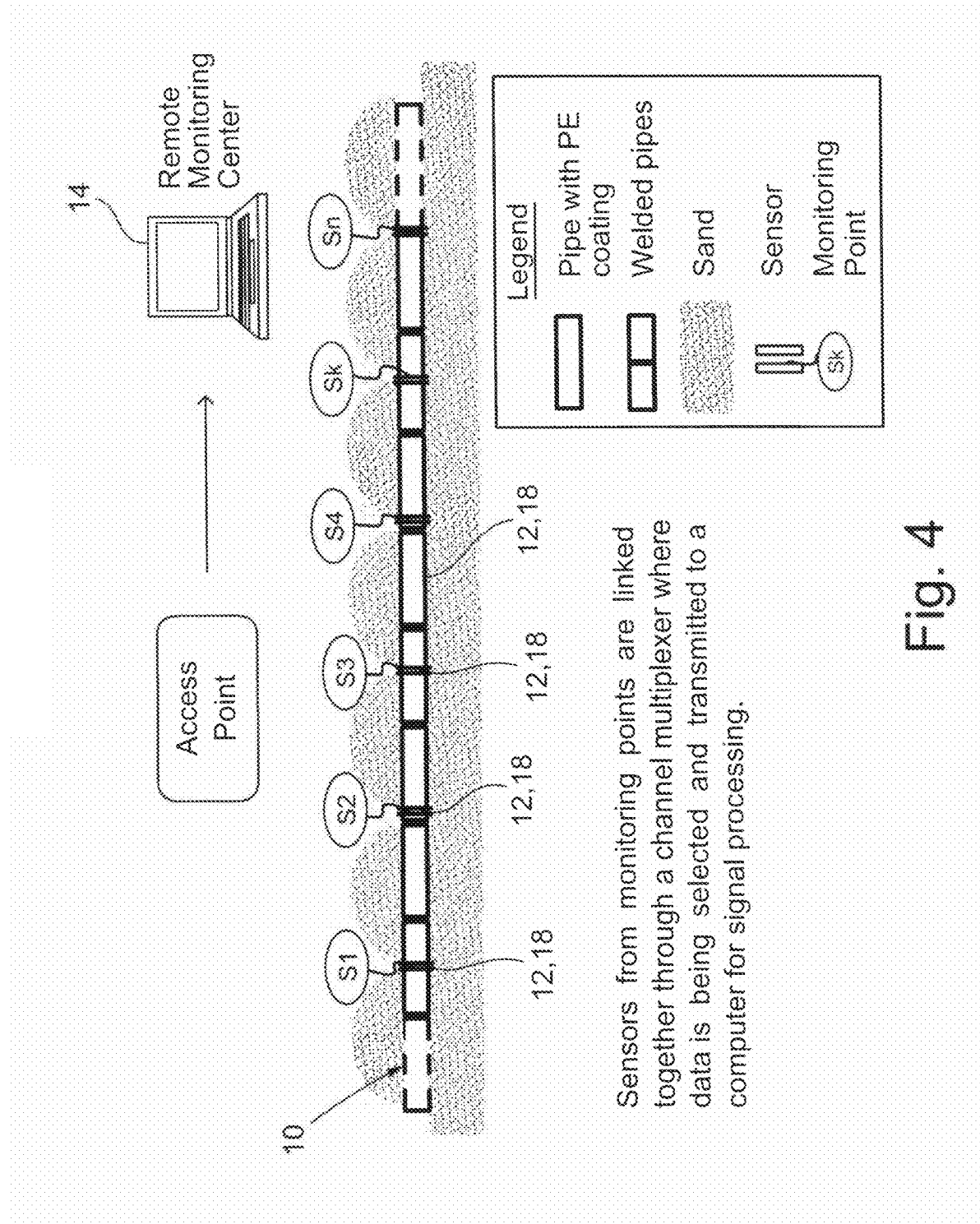
FIG. 4 shows an embodiment example of the guided-wave system for the non-destructive monitoring of deformations extending along a pressurized pipeline.
Figure 5:
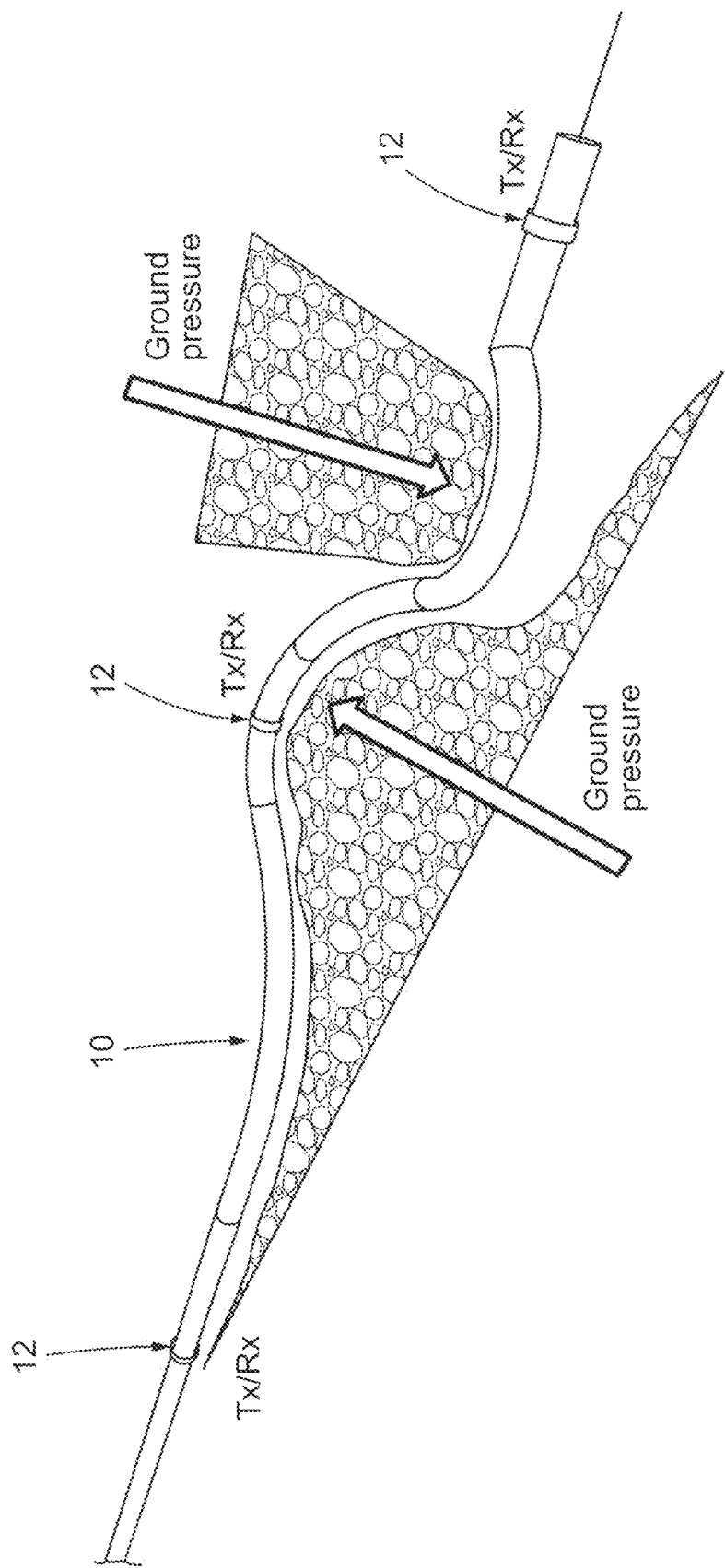
FIG. 5 shows an external deformation of a pipeline that can be detected with guided-wave sensors according to the invention.
Figure 6:
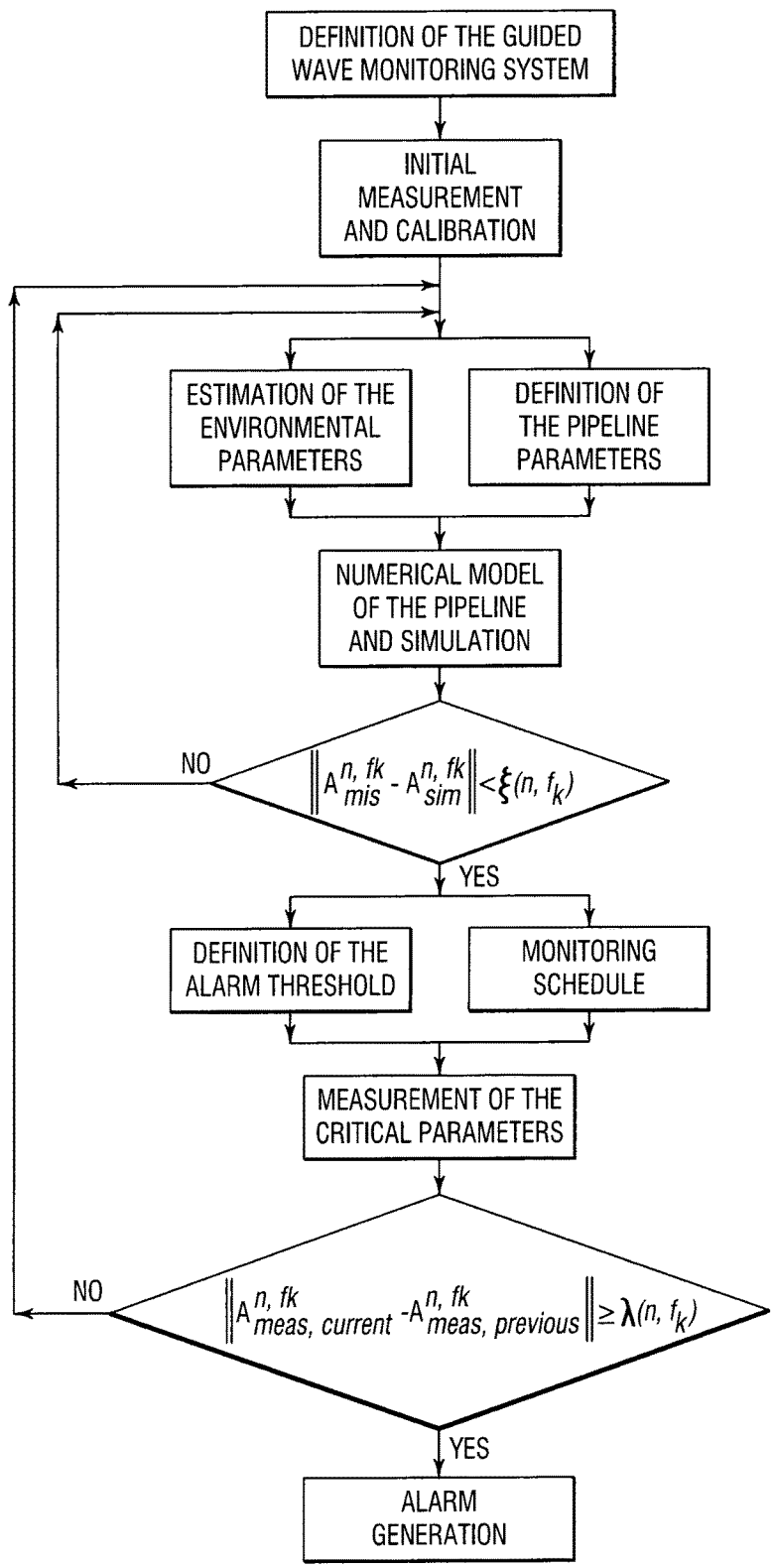
FIG. 6 is a block scheme which shows the phases of the continuous remote guided-wave monitoring method of pressure pipelines according to the present invention.

With reference to the installation scheme of FIGS. 4 and 5 and the flow chart of FIG. 6, the continuous remote monitoring method according to the present invention is composed of the following phases:

1. Definition of the monitoring points. N autonomous measurement $S_n$ stations 18 are installed on the pipeline 10, with n=1, ..., N, each equipped with a guided wave sensor 12 (magnetostrictive or piezoelectric) capable of operating in both pulse-echo mode and pitch-catch mode. A remote control unit 14 controls the sensors 12 and memorizes the data measured for the appropriate subsequent processing. The sensors 12 are installed at a predefined distance D, in the order of 10 meters so that the guided wave generated by a certain sensor 12 is capable of reaching the adjacent sensors 12.

2. Initial measurement and calibration. Measurements are carried out in multi-frequency $f_k$, with k=1, ..., K, on each section of pipeline 10A delimited by a pair of sensors 12A, 12B. Each of said sensors 12A, 12B registers both the echo produced by possible discontinuities present in the section of pipeline 10A considered, and also the signal generated by adjacent sensors 12 and transmitted through the section of pipeline 10A considered. The data measured are stored in a vector $A_{meas}^{n, fk}$.

3. Setup cycle of the numerical model and simulation. The generation and propagation of the guided waves are simulated on each section of pipeline 10A using a finished element model (FEM) capable of reproducing the measurement system and signals measured. For this purpose, it is necessary to know both the definition of the parameters of the pipeline 10 (geometry, material, thickness and diameter of the pipeline and its coating), and also the assessment of the environmental parameters either stable or subject to variation with time (laying depth, composition of the soil, ground pressure). The results of the simulation are stored in a simulated data vector $A_{sim}^{n, fk}$ and compared with the measured data vector $A_{meas}^{n, fk}$. The procedure is repeated, suitably modifying the environmental parameters until the deviation value $\|A_{meas}^{n, fk} - A_{sim}^{n, fk}\|$ between the measured data $A_{meas}^{n, fk}$ and the simulated data $A_{sim}^{n, fk}$ is lower than a predefined threshold value $\epsilon(n, f_k)$ which takes into account measurement errors and modeling errors.

4. Definition of the alarm thresholds and monitoring schedule. Using the finished element model of the pipeline-external means system defined in phase 3, the variation in the environmental parameters and parameters of the pipeline 10 significant for the integrity of the pipeline 10 itself, are simulated. In particular, the origination and growth of defects, the creation and growth of corrosion areas, the formation and growth of deposit areas, the variation in the pipe-coating coupling and the variation in the pressure exerted by the ground, are simulated, considering both small and large variations that can deform the pipeline 10 and cause its breakage. The results of the simulations allow the following parameters to be quantified:

the deviation in the signals in relation to the variations considered and consequently defining respective alarm thresholds $\lambda(n, f_k)$;

the deviation rate of the signals in relation to the variations considered and consequently temporarily planning the subsequent measurement (monitoring schedule).

5. Verification of the integrity of the measurement system and measurement of the parameters. After verifying the integrity of the measurement system, the measurement is provided in all points of the pipeline envisaged with the same procedures as the initial measurement. The results of the measurement are stored in the measured data vector $A_{sim}^{n, fk}$.

6. Measurement verification: repeating the cycle or alarm generation. The results of a certain current measurement $A_{meas,current}^{n, fk}$ are compared with those of the previous measurement $A_{meas,previous}^{n, fk}$. If the deviation $\|A_{meas,current}^{n, fk} - A_{meas,previous}^{n, fk}\|$ does not exceed any of the predefined alarm thresholds $\lambda(n, f_k)$, the simulation-measurement cycle is repeated, updating the numerical model of the pipeline-means system on the basis of the new measured data, defining new alarm thresholds $\lambda(n, f_k)$ and planning the subsequent measurement. When the deviation value $\|A_{meas,current}^{n, fk} - A_{meas,previous}^{n, fk}\|$ exceeds the predefined alarm threshold $\lambda(n, f_k)$, this indicates that there are critical variations in the state of the pipeline 10, thus requiring further verifications and analyses.

More specifically, the monitoring of deformations of the pipeline 10 due to internal or external pressure variations is effected by exploiting, before the possible breakage of said pipeline 10 occurs, the partial or total loss of the elasticity of the pipeline itself in the area affected by the pressure variations. On a section of pipeline 10A on which a transmitting sensor 12A and a receiving sensor 12B are installed, at a predefined distance D, this condition is revealed with one or more of the following variations in the pulse transmitted by the transmitting sensor 12A and received by the receiving sensor 12B:

variation in the transit time of the pulse through the section of pipeline 10A;

variation in the pulse width directly depending on the variation in the tensional state of the pipeline 10, without frequency modifications;

partial propagation of the guided wave through the section of pipeline 10A or lack of propagation of the guided wave through such section of pipeline 10A.

Figure 7:
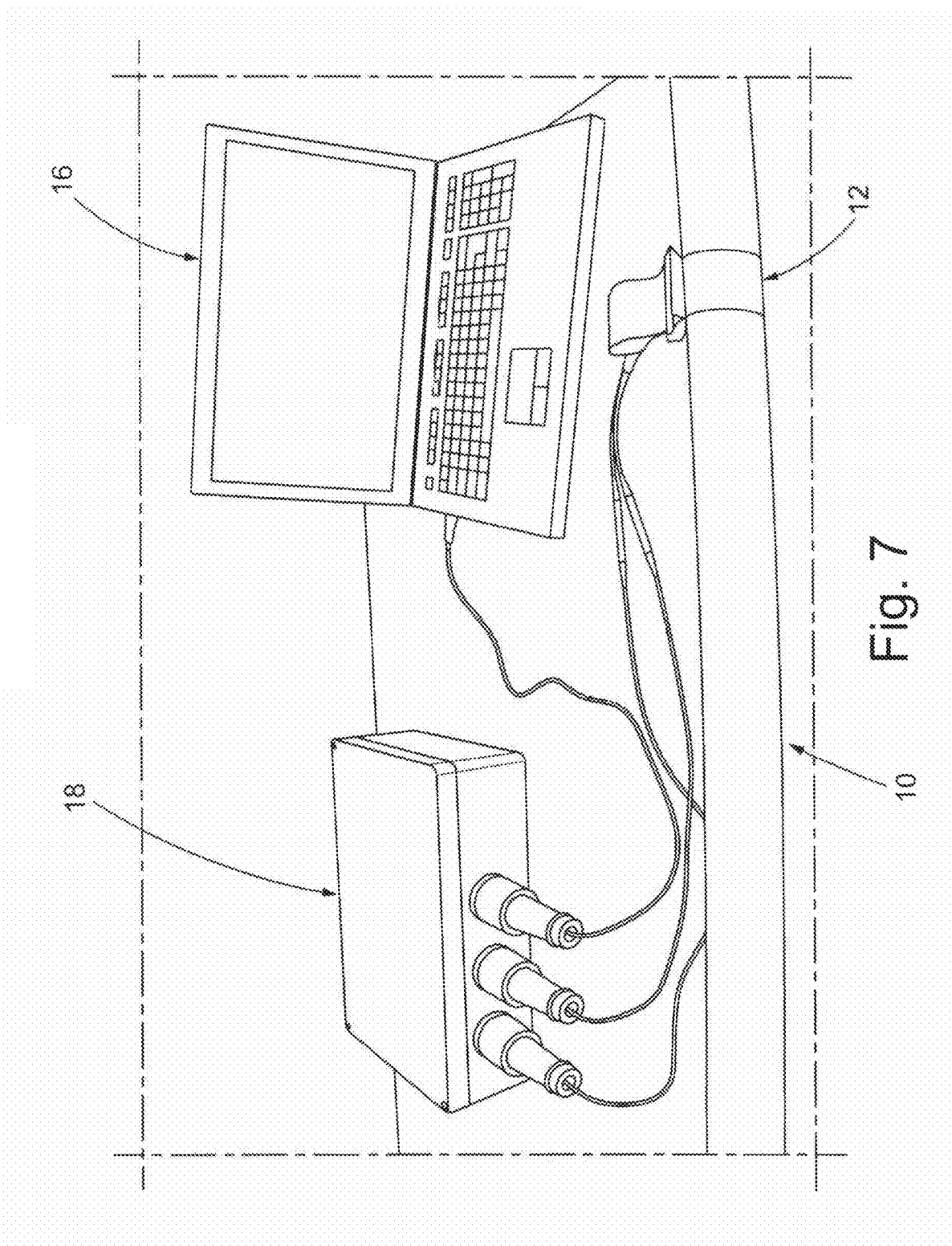
FIG. 7 shows the instruments of the continuous remote guided-wave monitoring system according to the present invention, in particular a sensing apparatus known as "RECOMS" (REmote COntrolled Magnetostrictive Sensor)

From an experimental point of view, both numerical simulations ad experimental measurement campaigns were carried out in the laboratory and also in gas plants using guided wave systems. A prototype of the sensor 18 was also designed and constructed, called "RECOMS" (REmote COntrolled Magnetostrictive Sensor) capable of generating and detecting guided waves, energetically autonomous and controllable by the remote control unit 14 through a wireless network (FIG. 7). The carried out experiments showed that guided waves are effective for monitoring pipelines 10 for the transportation of pressurized fluids and are capable of detecting both timely-local variations, as is the case with monitoring systems of the known type, and extensive variations in the tensional state and/or deformations of the pipeline 10, which is the innovative feature of the present invention.

More specifically, FIG. 4 shows a monitoring system according to the invention, that can be used for the monitoring of "oil & gas" pipelines inaccessible to control by means of Intelligent PIG systems. The system comprises a plurality of sensors 12, for example of the magnetostrictive type, that can be installed along the pipeline 10 and connected to each other and with the remote control unit 14 through a wireless network of the GSM or microwave type.

In particular, the system according to the invention is composed of a remote control unit 14, one or more local control devices 18 connected to said remote control unit 14 via wireless connection and sensors 12 in direct contact with the pipeline 10 to be monitored, each sensor 12 being wire-connected to at least one local control device 18. The system is capable of generating, in transmission mode, and detecting, in reception mode, guided waves of the torsional type and receiving commands and transmitting the results of the wave measurement to a computer 16 connected directly to each local control device 18, as illustrated in FIG. 7, and/or to the remote control unit 14 for managing the monitoring of the pipeline 10, as represented in FIG. 4. Each local control device 18 is powered by a rechargeable battery, thus providing the possibility of using a recharging circuit supplied from an "energy harvesting" system capable of ensuring the energy supply of the system for long periods of use also in remote sites. The system according to the invention is configured for being used in an ATEX environment (ATmospheres et EXplosibles) according to the directive 94/9/CE, i.e. also in areas subject to the risk of explosion.

Figure 8:
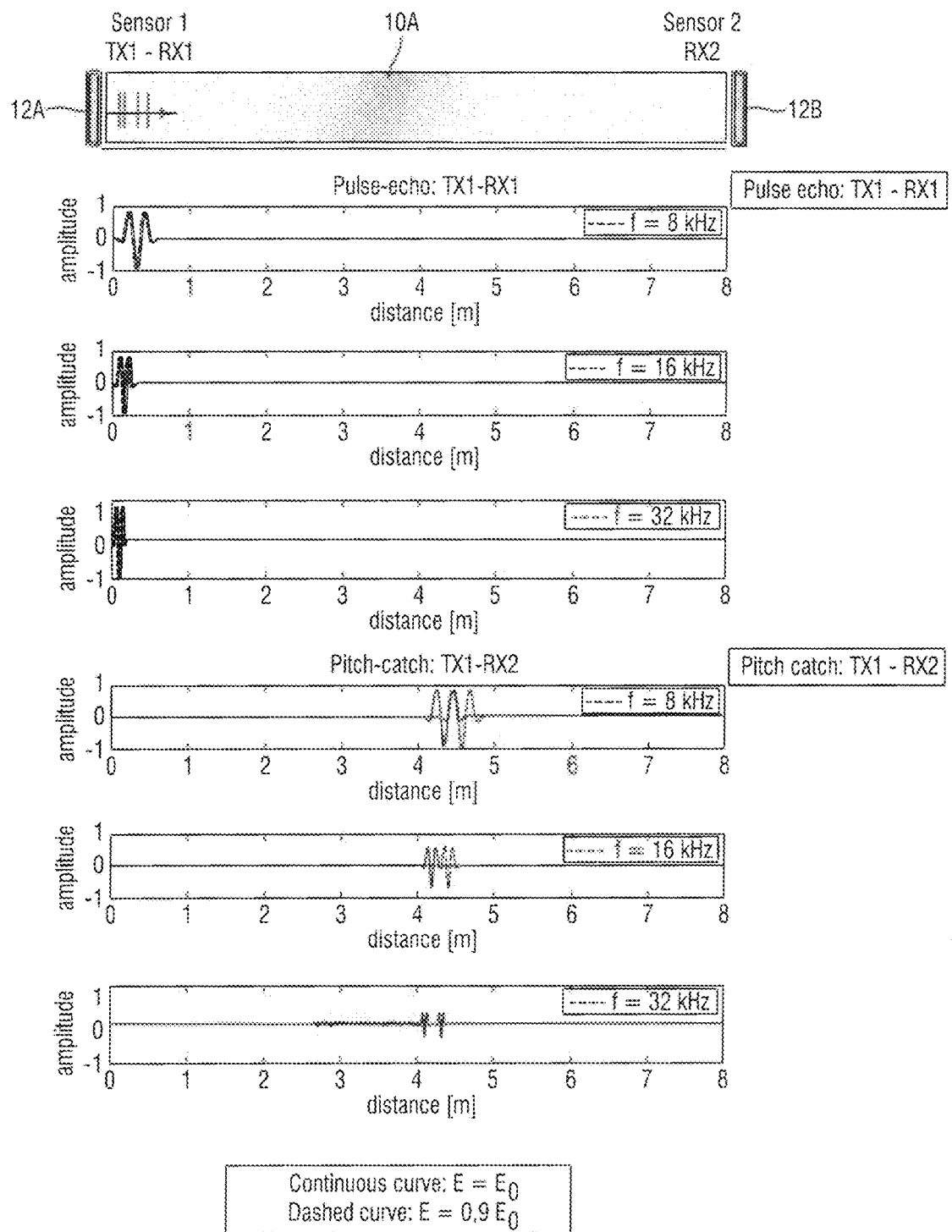
FIG. 8 shows a numerical simulation of the variation in the tensional state of the pipeline, with the response of the torsional guided-wave system in the case of carbon steel in the elastic range (continuous curve) and carbon steel in the elastic-plastic range (dashed curve) over the whole section of pipeline between two guided-wave sensors.
Figure 9:
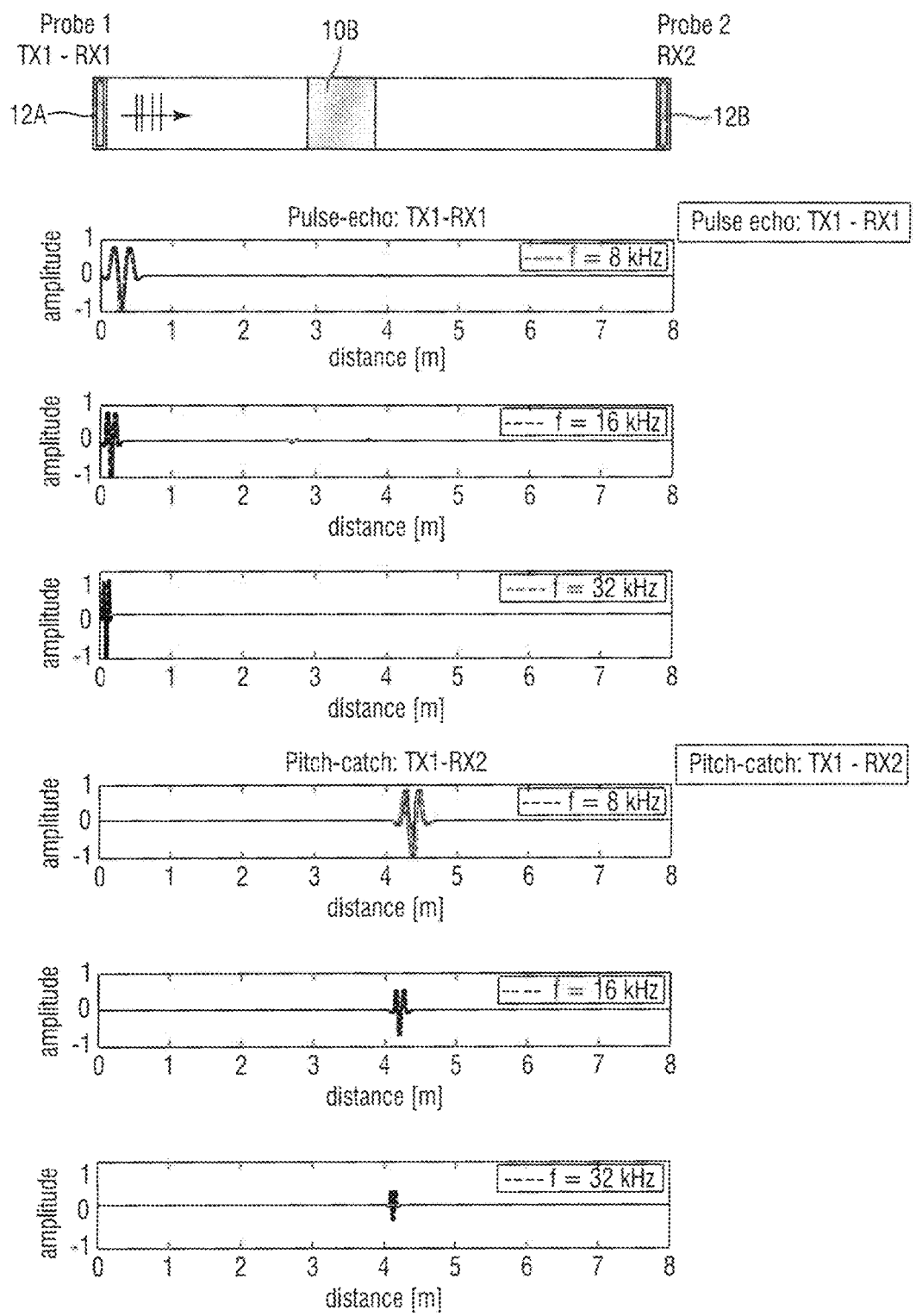
FIG. 9 shows a numerical simulation of the variation in the tensional state of the pipeline, with the response of the torsional guided-wave system in the case of carbon steel in the elastic range (continuous curve) and carbon steel in the elastic-plastic range (dashed curve) over a limited section of pipeline between two guided-wave sensors.

FIGS. 8 and 9 show the results of a simulation, effected using a finished element model (FEM), relating to the response of the guided wave system to a variation in the tensional state of a section of pipeline 10A surveyed by two sensors 12A and 12B. The first sensor 12A, operating in both TX mode and RX mode, transmits pulses to torsional guided waves at different frequencies and, in pulse-echo mode, it reveals their possible reflection due to the presence of discontinuities along the pipeline 10. The second sensor 12B reveals, in pitch-catch mode with the first sensor 12A, the pulses transmitted by the first sensor 12A. The reference state for the pipeline 10 is that for functioning under ordinary conditions, with the operating point of the steel in the elastic range. The variation is assumed, of the tensional state of a section of pipeline that brings the operating point within the elastic-plastic area (see FIG. 2).

With reference to FIG. 8, relating to the case in which the variation in the tensional state relates to the whole section of pipeline 10A included between the first sensor 12A and the second sensor 12B, the results obtained show that the guided wave system is capable of detecting the variation in the tensional state. In particular, it can be seen that, as expected, the first sensor 12A does not reveal any reflected signal whereas the second sensor 12B reveals the pulses transmitted by the first sensor 12A with a delay with respect to the expected value, the entity of the delay depending on the variation in the tensional state of the pipeline 10 and, at the same time, independent of the frequency of the pulse transmitted.

The same considerations can be made when (see FIG. 9) the variation in the tensional state relates only to a section of pipeline 10B included between the first sensor 12A and the second sensor 12B. The difference in the signals received by the two sensors 12A and 12B is that in this case, the first sensor 12A receives a reflected signal due to the presence of discontinuity, whereas the second sensor 12B receives the pulses with a lesser delay with respect to the case of FIG. 8.

Figure 10:
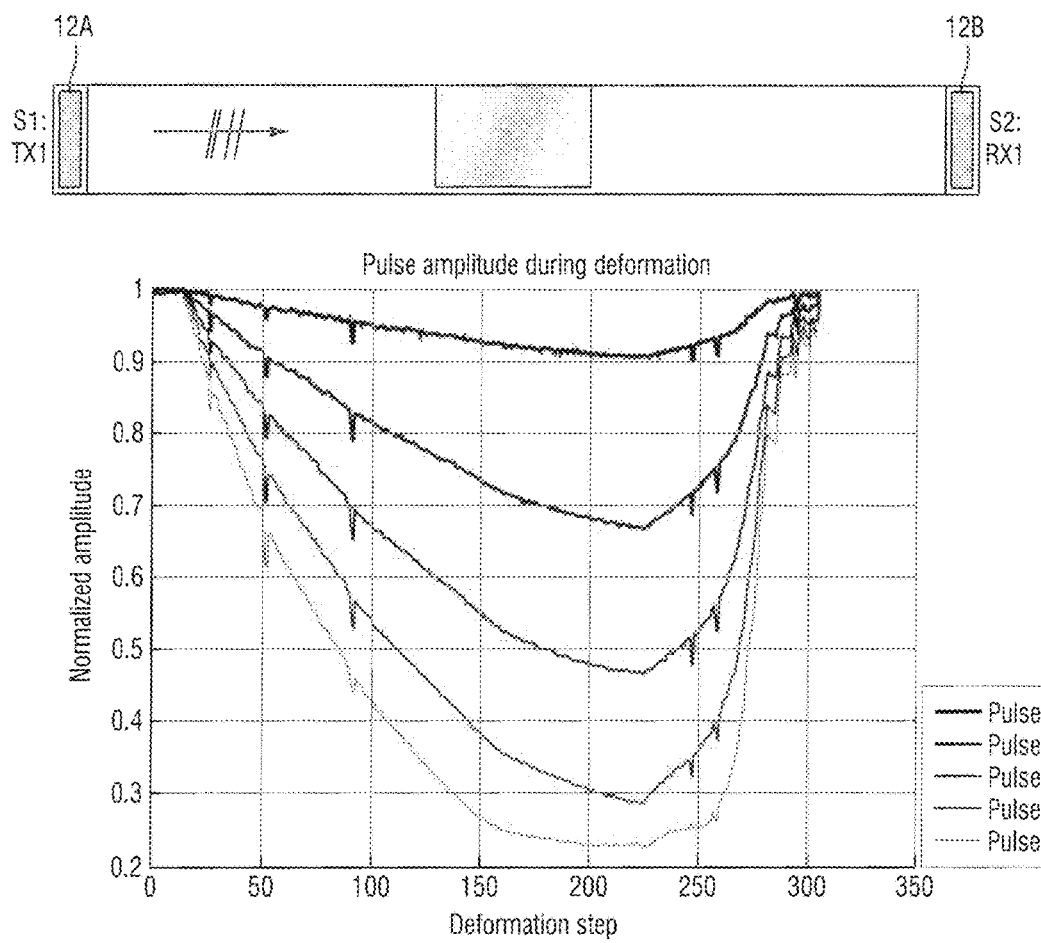
FIG. 10 shows the results of elastic deformation/external pressure experimental tests applied to a pipeline with continuous guided wave detection in pitch-catch mode.

FIG. 10 shows the results of the experimental laboratory tests carried out on a sample steel pipe having a diameter equal to 4 inches, a thickness equal to 3.6 millimeters and a length equal to 2 meters. In the central section having a length equal to 20 cm, the pipe is subjected to a variation in the external pressure (compression-decompression). Two sensors 12A (TX mode) and 12B (RX mode) for guided waves of the torsional type are installed at the ends of the pipe, functioning repeatedly with time in the pitch-catch mode. In particular, the first sensor 12A transmits a train of pulses at a constant frequency equal to 32 kHz, whereas the second sensor 12B receives each pulse transmitted by the first sensor 12A (pulse No1) and four replicas of the same pulse, due to the reflection from the ends of the pipe (pulse No2, No3, No4 and No5).

The reference state for the pipe is that in which no external pressure is exerted on the pipe itself: the pulse transmitted is received without being attenuated. This state corresponds in FIG. 10 to the normalized width having a value of 1. The experimental test consists in gradually increasing the external pressure (compression) exerted on the pipe until a maximum value is reached, subsequently gradually bringing the pipe back to the initial state by progressively decreasing the external pressure. The test has an overall duration of about 30 minutes, corresponding to 305 deformation steps of FIG. 10. The maximum pressure exerted on the pipe, obtained by applying a radial force of 40 kN, is such as to maintain the operating point of the steel within the elastic range (see FIG. 2). The results of the experimental test show that the guided wave system according to the present invention is effective in detecting and following with time, the deformation of the pipe due to the variation in the tensional state: the width of the pulses received decreases with an increase in the external pressure exerted, until a minimum value is reached, corresponding to the maximum value of the pressure exerted. By gradually bringing the tube back to the initial state, the width of the pulses received increases until it returns to the initial value.

It can thus be observed that the method and system for the continuous remote monitoring of deformations in a pressurized pipeline according to the present invention achieve the objectives previously indicated.

The method and system for the continuous remote monitoring of deformations in a pressurized pipeline according to the present invention thus conceived can in any case undergo numerous modifications and variants, all included in the same inventive concept. The protection scope of the invention is therefore defined by the enclosed claims.

The invention claimed is:

1. A method for continuous remote monitoring of deformations of a pipeline configured for transporting a pressurized fluid, the method comprising:
    installing a plurality of sensors on the pipeline, capable of transmitting and/or receiving guided waves generated in a form of elastic vibrations, wherein pairs of sensors are installed on respective sections of pipeline at a predefined distance;
    performing one or more initial calibration measurements on each section of pipeline, wherein each of said initial calibration measurements is performed with a generation and propagation of guided waves by at least one sensor, and wherein respective measured data are stored in a measured data vector ($A_{meas}^{n,\,fk}$);

simulating the generation and propagation of guided waves on each section of pipeline, using a numerical model based on specific parameters typical of the pipeline and of an environment in which said pipeline is installed, wherein respective simulated data are stored in a simulated data vector ($A_{sim}^{n, fk}$);

repeating the simulating until a deviation value ($\|A_{meas}^{n, fk} - A_{sim}^{n, fk}\|$) between the measured data ($A_{meas}^{n, fk}$) and the simulated data ($A_{sim}^{n, fk}$) is lower than a predefined threshold value ($\epsilon(n, f_k)$);

simulating a variation in said parameters, using said numerical model, so as to obtain values of said parameters which can jeopardize an integrity of the pipeline;

evaluating the deviation value ($\|A_{meas}^{n, fk} - A_{sim}^{n, fk}\|$) between the measured data ($A_{meas}^{n, fk}$) and the simulated data ($A_{sim}^{n, fk}$) as a function of the variation in said parameters for defining respective alarm thresholds ($\lambda(n, f_k)$);

performing one or more effective measurements on each section of pipeline, wherein the measured data are stored in the measured data vector ($A_{sim}^{n, fk}$);

repeating the performing one or more effective measurements until a deviation value ($\|A_{meas,current}^{n, fk} - A_{meas,previous}^{n, fk}\|$) between a certain current measurement ($A_{meas,current}^{n, fk}$) and a previous measurement ($A_{meas,previous}^{n, fk}$) exceeds at least one of said alarm thresholds ($\lambda(n, f_k)$), a passing of at least one of said alarm thresholds ($\lambda(n, f_k)$) indicating that there are critical variations in a state of the pipeline; and detecting and localizing the critical variations in the state of the pipeline based on the deviation value ($\|A_{meas,current}^{n, fk} - A_{meas,previous}^{n, fk}\|$) passing the at least one of said alarm thresholds ($\lambda(n, f_k)$).

2. The method according to claim 1, wherein, when the deviation value ($\|A_{meas,current}^{n, fk} - A_{meas,previous}^{n, fk}\|$) between the certain current measurement ($A_{meas,current}^{n, fk}$) and the previous measurement ($A_{meas,previous}^{n, fk}$) does not exceed at least one of said alarm thresholds ($\lambda(n, f_k)$), the simulating and the performing the effective measurements are repeated, updating the numerical model according to new measured data and defining new alarm thresholds ($\lambda(n, f_k)$).

3. The method according to claim 1, further comprising evaluating a rate of the deviation value ($\|A_{meas}^{n, fk} - A_{sim}^{n, fk}\|$) between the measured data ($A_{meas}^{n, fk}$) and the simulated data ($A_{sim}^{n, fk}$) as a function of the variation in said parameters, thus allowing time scheduling of the measurement steps.

4. The method according to claim 1, wherein said parameters typical of the pipeline comprise geometry, material, thickness and diameter of said pipeline and its coating.

5. The method according to claim 1, wherein said parameters of the environment in which the pipeline is installed comprise laying depth of said pipeline, composition of soil, and pressure of the soil.

6. The method according to claim 1, wherein the simulating the variation in said parameters comprises simulating:
a formation and growth of defects in the pipeline,
a formation and growth of corrosion areas,
a formation and growth of deposit areas,
a variation in a pipe-coating coupling, and
a variation in pressure exerted by soil, considering both small and large variations capable of deforming said pipeline and causing its breakage.

7. The method according to claim 1, wherein said numerical model is a finite element method (FEM).

8. The method according to claim 1, wherein said predefined distance is of about 10 meters, so that a guided wave generated by a certain sensor is capable of reaching adjacent sensors.

9. The method according to claim 1, wherein said guided waves are generated in the form of elastic vibrations of a torsional type, with frequencies within a range of 4 kHz to 128 kHz.

10. The method according to claim 1, wherein the monitoring of deformations in the pipeline due to internal or external pressure variations is performed by exploiting, before a possible breakage of said pipeline, a partial or total loss of elasticity of said pipeline in an area subjected to pressure variations, with one or more of the following variations in a pulse transmitted by a first sensor and received by a second sensor through a respective section of pipeline:
variation in passage time of the pulse through the respective section of pipeline;
variation in amplitude of the pulse directly depending on a variation in tensional state of the pipeline, without frequency modifications; and
partial propagation of a guided wave through the respective section of pipeline or lack of propagation of the guided wave through the respective section of pipeline.

* * * * *